US009138299B2

(12) United States Patent
Van Lierde et al.

(10) Patent No.: US 9,138,299 B2
(45) Date of Patent: Sep. 22, 2015

(54) METHOD AND SYSTEM FOR ESTABLISHING THE SHAPE OF THE OCCLUSAL ACCESS CAVITY IN ENDODONTIC TREATMENT

(75) Inventors: Carl Van Lierde, Meerbeke (BE);
Veerle Pattijn, Kessel-Lo (BE);
Paul-Henri Valloton, Pampigny (CH)

(73) Assignees: MAILLEFER INSTRUMENTS HOLDING SARL, Ballaigues (CH);
DENTSPLY IMPLANTS NV, Hasselt (BE)

( * ) Notice: Subject to any disclaimer, the term of this patent is extended or adjusted under 35 U.S.C. 154(b) by 18 days.

(21) Appl. No.: 14/117,124

(22) PCT Filed: Dec. 12, 2011

(86) PCT No.: PCT/EP2011/072475
§ 371 (c)(1),
(2), (4) Date: Nov. 12, 2013

(87) PCT Pub. No.: WO2012/155998
PCT Pub. Date: Nov. 22, 2012

(65) Prior Publication Data
US 2014/0322664 A1 Oct. 30, 2014

(30) Foreign Application Priority Data
May 13, 2011 (GB) .................... 1108002.5

(51) Int. Cl.
*G06K 9/00* (2006.01)
*A61C 5/02* (2006.01)
(Continued)

(52) U.S. Cl.
CPC .............. *A61C 5/023* (2013.01); *A61B 5/055* (2013.01); *A61B 6/032* (2013.01); *A61B 8/14* (2013.01);
(Continued)

(58) Field of Classification Search
CPC ........ A61C 13/0004; A61C 5/02; A61C 5/04; A61C 5/023; A61B 19/50; A61B 19/5244; A61B 2019/262; A61B 2019/505; A61B 2019/507
USPC .......................................... 382/128
See application file for complete search history.

(56) References Cited

U.S. PATENT DOCUMENTS 6,197,410 B1 * 3/2001 Vallittu et al. ............. 428/292.1
6,334,775 B2 * 1/2002 Xu et al. .................... 433/228.1
(Continued)

FOREIGN PATENT DOCUMENTS

WO 2011/019846 A1 2/2011
WO 2011/101447 A2 5/2011

OTHER PUBLICATIONS

J. Dong et al., "Tool selection and path control for automated anterior teeth coronal canal treatment preparation", 2005 ASME International Mechanical Engineering Congress and Exposition, IMECE 2005, American Society of Mechanical Engineers, US; Orlando, FL, USA, vol. 16-1, Jan. 1, 2005, pp. 109-117.

(Continued)

*Primary Examiner* — Ali Bayat
(74) *Attorney, Agent, or Firm* — Young & Thompson

(57) ABSTRACT

A computer based method and system for defining and representing a shape and geometry of an occlusal access cavity to the tooth roots prior to endodontic treatment, include the step or elements for: loading onto the computer information of the geometry of a tooth obtained via one or more imaging techniques, creation of a 3D computer model of the tooth, including its internal architecture, visualization of the computer model, visualization of the location(s) of the entrance(s) to root canal(s) relative to the tooths occlusal surface, and based on the locations of the root canal orifices a shape of the access cavity is calculated.

26 Claims, 6 Drawing Sheets

(51) Int. Cl.

| | |
|---|---|
| *G06F 19/00* | (2011.01) |
| *G06T 19/20* | (2011.01) |
| *A61B 19/00* | (2006.01) |
| *A61B 5/055* | (2006.01) |
| *A61B 6/03* | (2006.01) |
| *A61B 8/14* | (2006.01) |
| *G06F 19/12* | (2011.01) |
| *A61C 13/00* | (2006.01) |

(52) U.S. Cl.
CPC . *A61B 19/50* (2013.01); *A61C 5/02* (2013.01); *G06F 19/12* (2013.01); *G06F 19/3437* (2013.01); *G06T 19/20* (2013.01); *A61B 19/5244* (2013.01); *A61B 2019/262* (2013.01); *A61B 2019/505* (2013.01); *A61B 2019/507* (2013.01); *A61C 13/0004* (2013.01); *G06T 2210/41* (2013.01)

(56) References Cited

U.S. PATENT DOCUMENTS

| | | | |
|---|---|---|---|
| 2005/0227198 A1* | 10/2005 | Martin | 433/31 |
| 2011/0038514 A1* | 2/2011 | Weigl | 382/128 |
| 2013/0040267 A1* | 2/2013 | Bergheim et al. | 433/216 |

OTHER PUBLICATIONS

Ricardo Caicedo et al., "Guidelines for Access Cavity Preparation in Endodontics", Dental CE Digest, Jan. 1, 2006, pp. 1-8.

Clifford J. Ruddle, "Endodontic Access Preparation: The Tools for Success", Just in Time Online Education, Dental Products Report, Oct. 1, 2007, pp. 1-9.

L. R. Wilcox et al., "Molar Access: Shape and Outline According to Orifice Locations", Journal of Endodontics, Lippincott Williams & Wilkins, Philadelphia, PA, US, vol. 15, No. 7, Jul. 1, 1989, pp. 315-318.

Desmond M. Germans et al., "Measuring in Virtual Reality: A Case Study in Dentistry", IEEE Transactions on Instrumentation and Measurement, IEEE Service Center, Piscataway, NJ, US, vol. 57, No. 6, Jun. 1, 2008, pp. 1177-1184.

J. Dong et al., "Theories and algorithms for 3-D root canal model construction", Computer Aided Design, Elsevier Publishers BV., Barking, GB, vol. 37, No. 11, Sep. 15, 2005, pp. 1177-1189.

Yuan Gao et al., "An Application Framework of Three-dimensional Reconstruction and Measurement for Endodontic Research", Journal of Endodontics, Basic Research—Technology, Lippincott Williams & Wilkins, Philadelphia, PA, US, vol. 35, No. 2, Feb. 1, 2009, pp. 269-274.

Kleoniki Lyroudia et al., "Virtual Endodontics: Three-Dimensional Tooth Volume Representations and their Pulp Cavity Access", Journal of Endodontics, Lippincott Williams & Wilkins, Philadelphia, PA, US, vol. 28, No. 8, Aug. 1, 2002, pp. 599-602.

Peter Spili et al., "The Impact of Instrument Fracture on Outcome of Endodontic Treatment", Journal of Endodontics, vol. 31, Issue 12, Dec. 2005, pp. 845-850.

David Kan, "Medico-legal aspects of endodontic treatment", Medico-Legal Corner, Hong Kong Dental Journal 2004; 1:99-100.

International Search Report dated Sep. 13, 2012, corresponding to PCT/EP2011/072475.

* cited by examiner

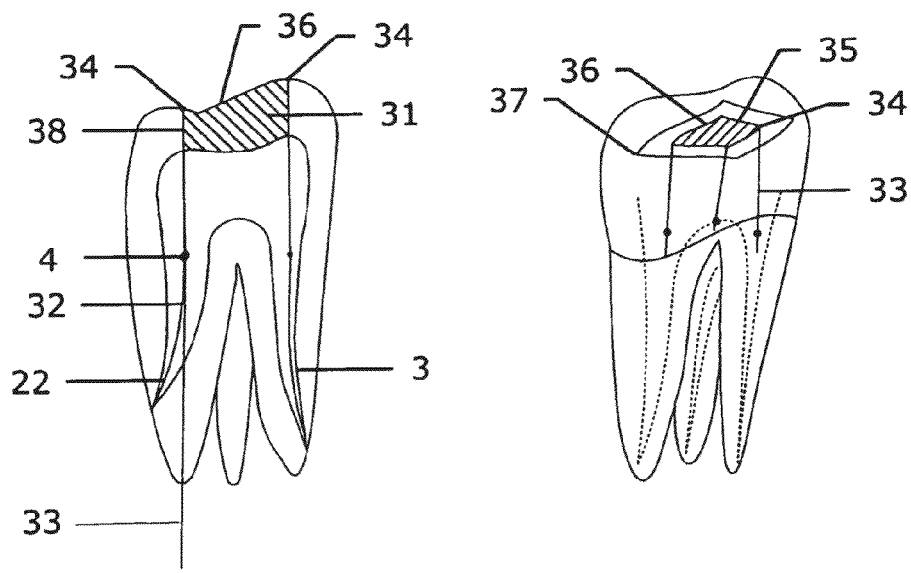
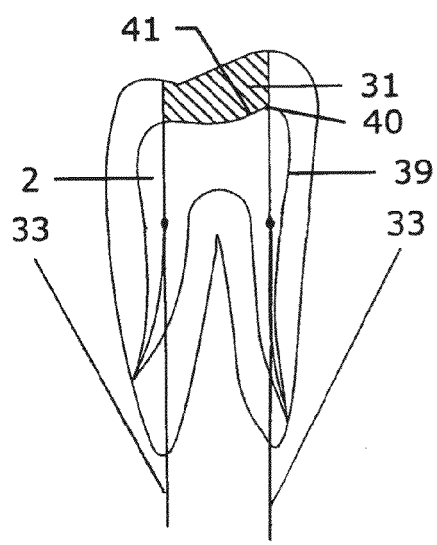
Fig. 7
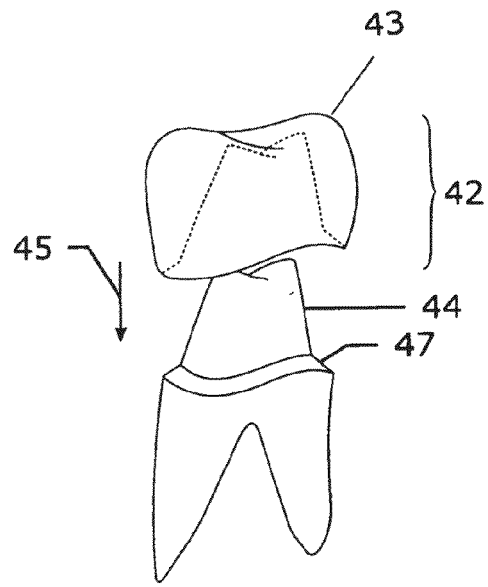
Fig. 6
Fig. 8

METHOD AND SYSTEM FOR ESTABLISHING THE SHAPE OF THE OCCLUSAL ACCESS CAVITY IN ENDODONTIC TREATMENT

FIELD OF THE INVENTION

The present application relates to methods, computer programs and software, tools and systems for establishing the shape of the occlusal access cavity in endodontic treatment.

BACKGROUND

During endodontic root canal treatment, the tooth pulp and nerves are removed from the root canals when they have been injured or are diseased. Treatment can be performed surgically by removing the apex of the tooth root (aka an apicoectomy) and sealing (obturating) the root canal via an access hole made through the jaw bone of the patient. However the more conventional treatment approach is to open the tooth occlusally, create a cavity (including the pulp chamber) providing access to the canal orifices, remove the diseased pulp and nerves, remove the diseased dentin by using specialized instruments such as endodontic files) to mechanically shape the root canals, clean and disinfect the root canals by means of specific irrigation media, and seal and obturate them to prevent any bacterial re-access to the treated zone.

DESCRIPTION OF THE RELATED ART

A well known problem during this type of approach is related to fracture of the instruments. According to literature ("The Impact of Instrument Fracture on Outcome of Endodontic Treatment", Peter Spilli, BSc, BDSc, Peter Parashos, MDSc, PhD, and Harold H. Messer, MDSc, PhD, JOE— Volume 31, Number 12, December 2005 pp 845-850) the prevalence of fractured endodontic hand instruments has been reported to range from 1 to 6%. It is the second most important reason for medico-legal claims in endodontics and accounts for approx. 5.6% of all dental claims (Medico-Legal Aspects of Endodontic Treatment, David Kan, Hong Kong Dental Journal 2004; 1:99-100). In cases with a periapical lesion, retained fragments of endodontic instruments have been reported to reduce healing. One of the most common causes for instrument fracture is improper preparation of the occlusal cavity that provides access to the pulp chamber and the connected root canals. Often the size of the cavity is undersized or improperly shaped. This leads to improper bending of the instruments during removal of the pulp, ultimately resulting in instrument failure. In addition, the improper preparation of the access cavity may result in missing a main root canal e.g. the fourth mesio-buccal canal in a top molar tooth. Since the efficacy of the endodontic treatment is highly dependent on the extent to which the diseased/infected tissue is removed, missing a canal may eventually result in treatment failure. Ideally the access cavity must provide a straight line access and a glide path that helps the instruments to perform at maximum capability. Incomplete access increases the stress on the files and leads to breakage.

For the practitioner it is however very difficult to adequately prepare the access cavity because of limited visibility and because the location of the root canal orifices is mostly uncertain (in 3D) prior to the start of the treatment. Typically the practitioner drills into the tooth until a first access is realized into the pulp chamber. Subsequently this access is gradually extended while searching for the root canals. Without reliable information about the root canals, in particular their amount and the localization of their orifices in the floor of the pulp chamber, there is a large degree of likelihood that the access cavity will not be properly dimensioned. Moreover, in some cases too much of the healthy occlusal tissue may be removed, potentially compromising an easy prosthetic restoration of the tooth.

In the prior art it is known to use CT imaging to obtain a three dimensional visualization of the tooth and corresponding root canals. Patent application PCT/EP2011/052457 teaches a method and system for 3D digital endodontics characterized in that 3D imaging equipment such as a CT or MRI scanner, ultrasound or the like are used to digitize the ailing tooth or teeth, subsequently a 3D representation of the root canal system is extracted from the image data and visualized on a computer screen, and a surgical template is designed to guide the endodontic instruments to localize the root canal(s) intra operatively. In addition, the location of the root canal orifices is determined by extracting the root canal system from the image data e.g. by indicating points along the axis of the root canal in one or multiple slices of the image set. These points are connected and make up a 3D line graph representative of the root canal system of the tooth.

While this method provides information about the root canals and helps by means of a guide to localize the root canals intra operatively, it does not mention or teach how to prepare and shape the access cavity to the pulp chamber in such a manner that straight line access is realized for each of the identified root canals, without removing excess material from the tooth's occlusal surface. Hence, instrument fracture may still occur.

According to the current state of the art there is no way to optimize the shape of the access cavity in function of the prosthetic restoration (e.g. inlay, crown) of the tooth subsequent to the endodontic treatment.

Among the remaining prior art, there are some other solutions referring to the use of computer to improve the endodontic treatment. WO2011019846 discusses a dental handpiece with and integrated camera and computer that allows for pre-programmed procedural steps and feedback as the treatment proceeds. The computer transmits camera images and data retrieved from integrated sensors to the dental professional via an attached monitor. The described method and system however does not discuss shaping or preparing the access cavity to the pulp chamber, e.g. in order to prevent instrument fracture or optimize the prosthetic restorative capabilities after the endodontic intervention.

SUMMARY OF THE INVENTION

An object of the present invention is to provide a method, tools or system for defining and representing the shape and geometry of the occlusal access cavity to the tooth roots prior to endodontic treatment. Another object of the present invention is to provide a method, tools or system for transferring the information about the desired shape of the occlusal access cavity to the tooth of the patient during endodontic treatment.

The present invention seeks to reduce or overcome at least one of the problems of the prior art methods and devices.

According to the present invention, defining the shape and geometry of the occlusal access cavity to the tooth may be accomplished using a computer or a computer system such as a computer network. Information of the geometry (internal and external) of the tooth to be treated may be acquired via one or more imaging techniques. The nature of images (2D, 3D, surface information, volumetric information, etc.) used to capture the geometrical information about the tooth may vary as may the nature of the imaging technique used (X-ray, CT, MRI, ultrasound, etc.). Potentially, multiple imaging modalities may be combined.

The acquired information is used to create a 3D computer model of the tooth, including its internal architecture i.e. root canals and pulp chamber. The computer model may be visualized on any form of display device such as a computer screen, a projected display, a head mounted display, in sectional views or in a 3D representation such as a surface model or a volume rendering.

The location(s) of the entrance(s) to the root canal(s) (relative to the tooth's occlusal surface) as well as information about the 3D curvature of the root canal(s) are extracted from the computer model of the tooth. The level of automation of this step may vary. In one embodiment, the method and system is adapted, e.g. by providing suitable input means such as a keyboard, a keypad, a mouse pointer etc. and software to allow the user to input data. For instance, points along the root canal(s) may be indicated by any suitable means, e.g. via the graphical user interface or by entering their 3D coordinates numerically. According to another embodiment, feature recognition algorithms or the like are used by the method or system to discriminate the root canal(s) relative to the remainder of the tooth. Yet other embodiments may require the system to use a combination of user input and/or image processing tools and/or statistical data of tooth-root geometry.

It is a feature of the current invention that based on the determined locations of the root canal orifices a shape of the access cavity is calculated. The calculation may or may not take into account the information of the 3D curvature of the tooth and/or requirements relative to the desired prosthetic restoration of the tooth subsequent to endodontic treatment and/or requirements/limitations with respect to the use of endodontic instruments.

It is another feature of the present invention that based on the calculatedshape of the access cavity, an outline is calculated on the occlusal surface of the tooth indicating the surface boundaries of the access cavity on the occlusal side of the tooth. Means are provided for visualizing this outline on the display device such as the computer screen e.g. in an occlusal view of the tooth and transferred to the mouth of the patient e.g. by means of a custom made jig.

A significant advantage of the present invention is that clinicians are substantially aided in planning the root canal treatment by having unambiguous guidelines implemented on how to optimally shape the access cavity in function of patient specific information. The invention also constitutes a considerable saving in chair time given that the clinician can start the treatment knowing how many root canals must be cleaned, where to look and how to dimension the access cavity. There is no need for exploration during the treatment itself, nor is there any uncertainty left about whether or not all necessary root canals have been treated.

Another advantage of the current invention is that the access cavity can be easily prepared to assure straight line access to the root canals and minimal bending of the endodontic instruments to avoid their breakage.

These and further objects, features and advantages of the invention will become apparent from the following detailed description wherein reference is made to the figures in the accompanying drawings.

BRIEF DESCRIPTION OF THE FIGURES

The drawings described are only schematic and are non-limiting. In the drawings, the size of some elements may be exaggerated and not drawn on scale for illustrative.

FIG. 6 shows straight lines fitted through the respective 3D curves associated with the root canals of a tooth, intersecting with the occlusal surface of said tooth, thereby defining the outline of the access cavity on that surface in accordance with an embodiment of the present invention.

FIG. 7 shows straight lines fitted through the respective 3D curves associated with the root canals of a tooth, intersecting with the surface of the pulp chamber in accordance with an embodiment of the present invention. The connected intersection points thereby define the outline of the access cavity on the surface of the pulp chamber, the projection of which on the occlusal surface of the tooth defines the shape of the access cavity.

FIG. 8 shows a prepared tooth stump and the desired prosthetic reconstruction in the form of a dental crown.

DESCRIPTION OF PREFERRED EMBODIMENTS

Figure 1:
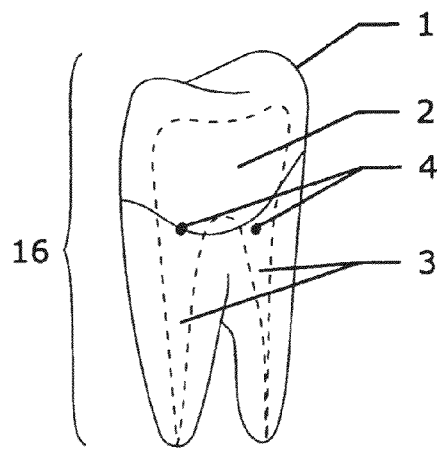
FIG. 1 shows a 3D computer model of a tooth with its internal architecture i.e. pulp chamber and root canals which can be used with the present invention.
Figure 2:
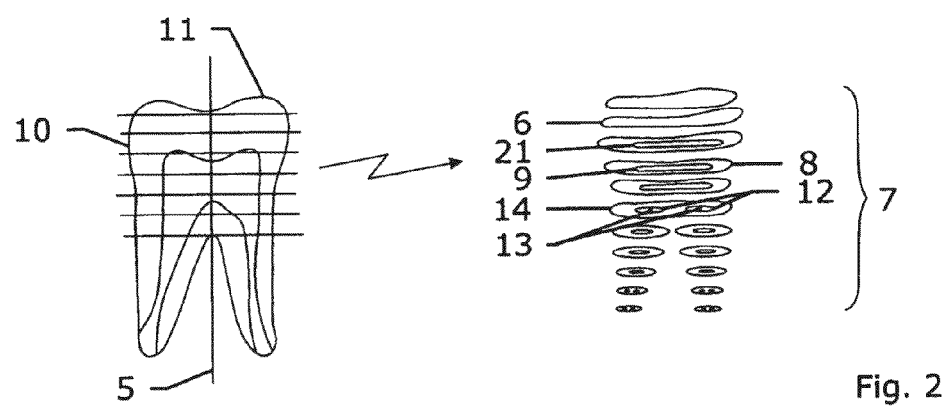
FIG. 2 shows a cross section of a tooth and a 2.5D representation of the same tooth by means of contours which can be used with the present invention.
Figure 3:
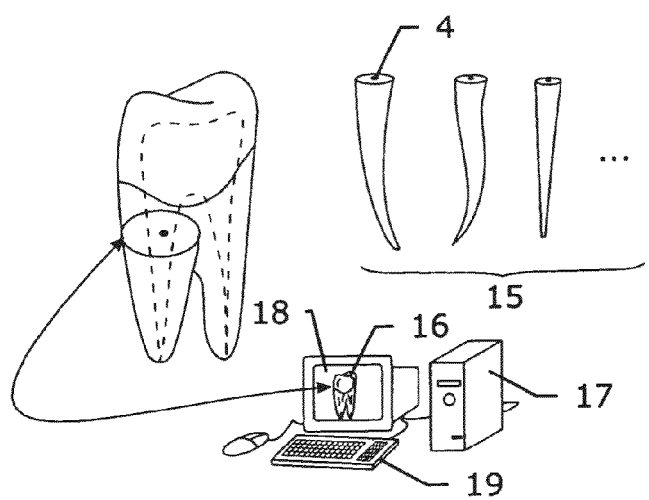
FIG. 3 shows a system for establishing the shape of the occlusal access cavity in endodontic treatment using feature recognition algorithms to identify the root canals and their respective entrances in accordance with an embodiment of the present invention.
Figure 4:
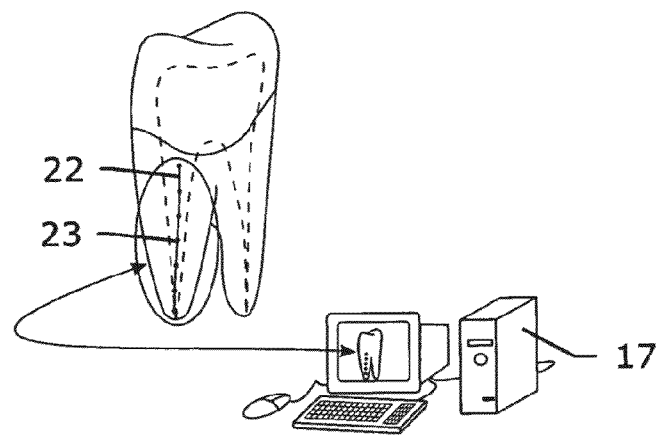
FIG. 4 shows a graphical user interface for indicating points along the root canal through which a 3D curve is fitted in accordance with an embodiment of the present invention.
Figure 5:
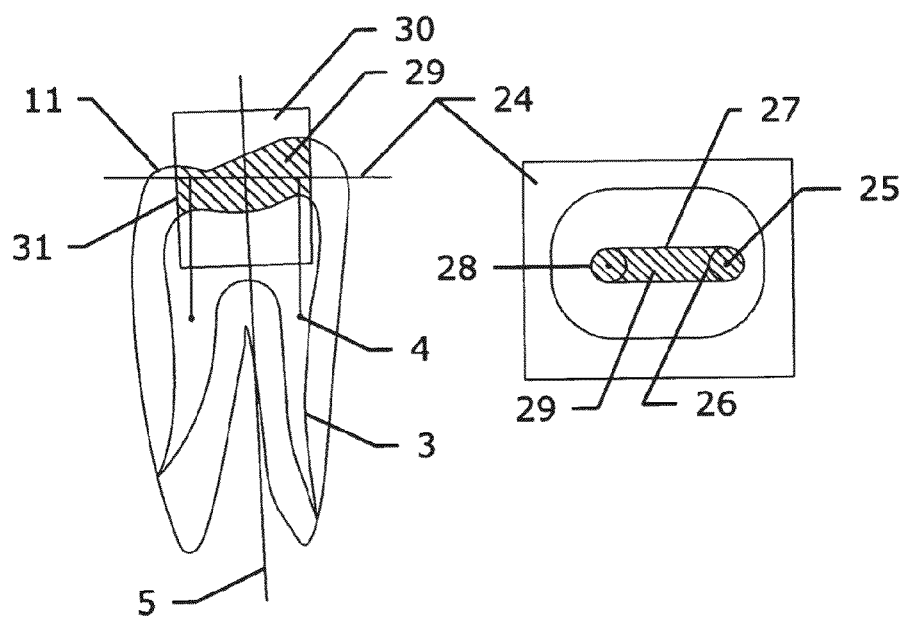
FIG. 5 shows a cross sectional and occlusal view of a tooth for which the calculated (recommended) access cavity has been determined in accordance with an embodiment of the present invention.
Figure 9:
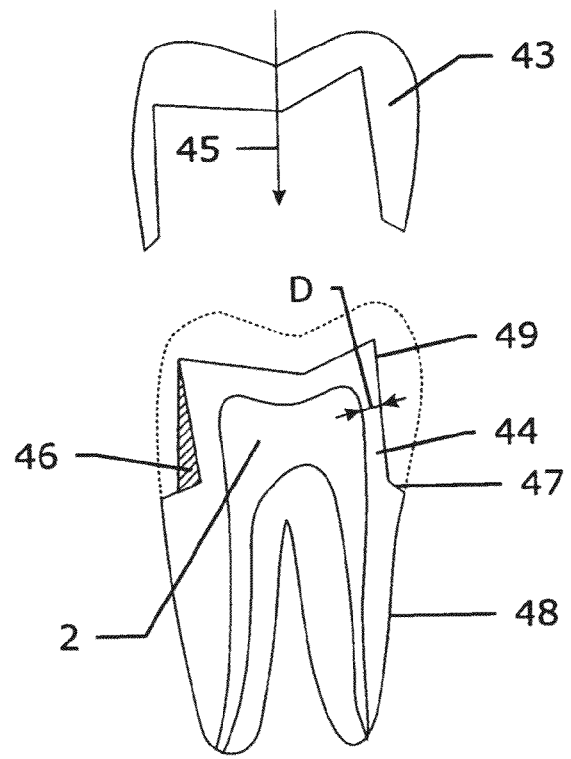
FIG. 9 shows a cross section of a crown and tooth stump, the latter which has been prepared with an undercut in relation to the direction of insertion of the crown in accordance with an embodiment of the present invention.
Figure 10:
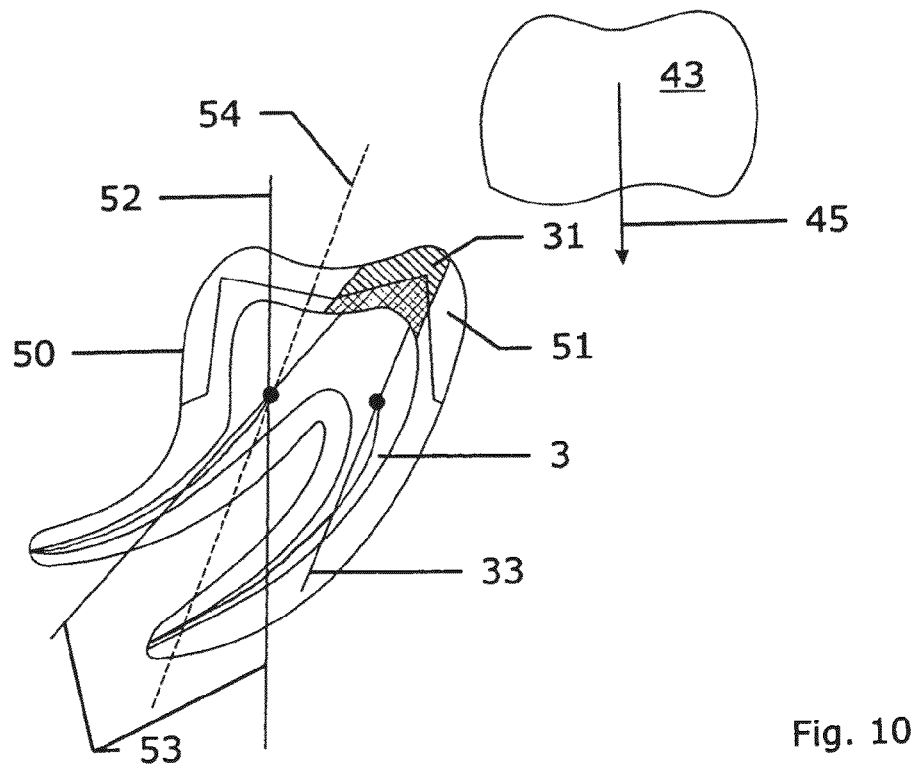
FIG. 10 shows a tooth to be prepared for receiving the (artificial) crown, with root canals substantially askew relative to the original crown in accordance with an embodiment of the present invention.
Figure 11:
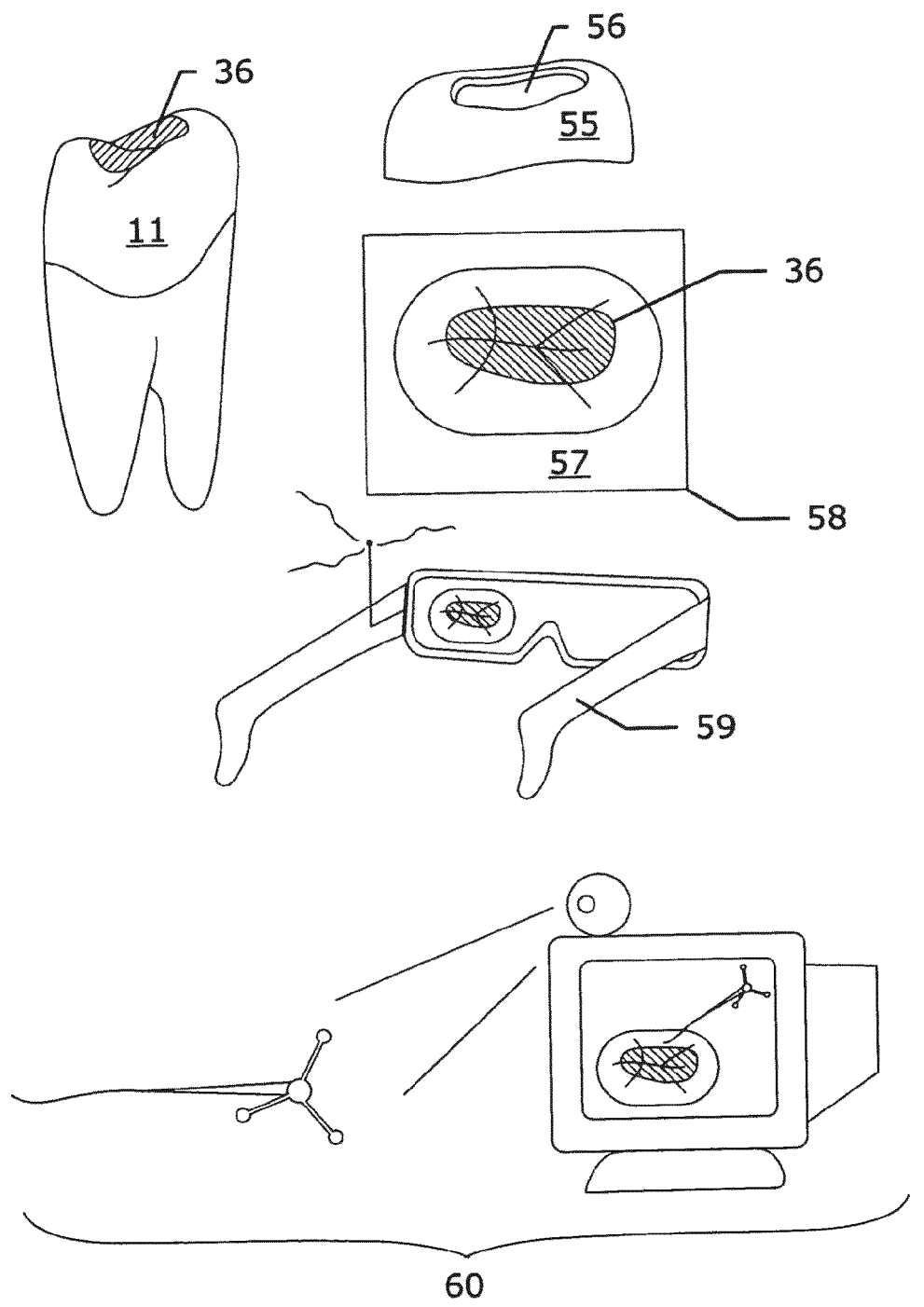
FIG. 11 shows a 3D computer model of tooth with the outline of the suggested access cavity shown on its occlusal surface and different means (i.e. jig, transparent, glasses and navigation system) for transferring said outline to the tooth in the mouth of the patient in accordance with an embodiment of the present invention.

The present invention will be described with respect to particular embodiments and with reference to certain drawings but the invention is not limited thereto but only by the claims.

According to a preferred embodiment of the invention a three-dimensional computer model (16) of the tooth (1) including the pulp chamber (2) and the root canals (3), is required and obtained. Tooth enamel, bone and soft tissue are visible. The method starts when said three-dimensional computer model (16) is available. In a first subsequent step, the locations of the root canal orifices (4) (relative to the tooth's occlusal surface) are extracted from the computer model (16) of the tooth (1). According to one approach, this step is fully automated. As an example, the automation consists of the following sequence of actions performed by the system (17). First, the apical-coronal (longitudinal) axis (5) of the tooth (1) is determined. This can be done e.g. based on the calculation of the principal axes of inertia of the tooth (1). Once, the main principal axis has been calculated, planar intersection curves (i.e. contours) (6) are calculated with the tooth representation equidistantly along said axis. The result is a set of contours giving a 2.5D representation (7) of the tooth (1). This set of contours consists in outer contours (8) representing the tooth surface (10) and inner contours (9) representing root canals (3) and pulp chamber (2). The locations of the entrance points (4) to the root canals are determined by screening the planar intersections (slices) (6) along the axis, in the apical direction of the tooth (1), starting at a given distance relative to the coronal (i.e. occlusal) surface (11) of the tooth. The transition from pulp chamber (2) to root canal(s) (3) is marked either by the fact that the area (21) enclosed by the inner contour (9) of the tooth (1) reaches a predetermined threshold value (as is typically the case for incisors) or by the fact that the inner contour (9) divides in multiple contours (12) (as typical in the case of a molar or premolar). The latter can occur at different levels along the longitudinal tooth axis (5) e.g. in case of three or more roots. Having determined the slices (14) that mark the transition between the pulp chamber (2) and the root canals (3), the locations of the root canal orifices (4) are given by e.g. the centers of gravity (13) of the inner contours corresponding to those slices.

According to another example the automation consists in the use of feature recognition algorithms by the system. Features (15) are mathematical representations (e.g. matrices) of the possible shapes of a tooth root canal (3). A feature is recognized for instance when a given correlation value becomes greater than a certain value. Once the feature (i.e. root canal) has been identified, its entrance is also known relative to the occlusal surface (11) of the tooth (1).

Using a different approach, the root canal orifices are given as an input to the system (17). This approach requires interaction with the end-user, which can be facilitated by the system (17) by means of a graphical user interface (18) that allows the user to indicate the relevant points (4) on the 3D computer model (16) directly. Alternatively the input may be given numerically by entering into the system (17) the coordinates of the entrance points e.g. via a keyboard (19).

In a second, optional step, information about the 3D curvature of the root canals (3) is extracted from the computer model (16) of the tooth (1). Hereto the midline (20) of every root canal (3) may be determined (semi-) automatically by the system (17). As in the previous step the calculation of these 3D midlines (20) may also be automated to various degrees. According to a simple implementation a 3D curve (22) is fitted through a number of points (23) along the root canal (3), whereby these points (23) have been given as input by the user into the system (17). More advanced implementations may use slices (6) as described previously to determine successive center points of gravity (14) for the contours (6) along the root(s) canals (3) and fit a curve. Other implementations are possible. With a 3D curve (22) associated with every root canal (3), 3D curvatures are yielded by applying the appropriate mathematical formulae.

In a third step, the system (17) determines the shape of the access cavity (31) to the pulp chamber (2) based on at least the locations of the entrances (4) to the root canals (3). According to one embodiment, a plane (24) is fitted through the occlusal surface (11) of the tooth (1). Next, the entrance points (4) to the root canals (3) are projected into that plane (24) according to a direction perpendicular to said plane (24). Around every projected entrance point (25) in the plane (24), a circle (26) is defined with a predefined diameter e.g. 100 μm. The circles (26) are then connected in the plane (24) with straight lines (27) in such a manner that all circles are engulfed by the resulting boundary (28), minimizing the enclosed surface area (29). In case of only one root canal (3) the boundary (28) will consist in a single circle. The boundary (28) is then extruded along the apico-coronal (longitudinal) axis (5) of the tooth (1) and the intersection (29) of the resulting 3D volume (30) with the 3D model (16) of the tooth (1) is calculated. The shape of the intersecting part (29) between the occlusal surface (11) and the pulp chamber (22) defines the shape of the (in this case parallel walled) access cavity (31).

According to another embodiment, the system (17) uses the additional information about the roots' 3D curvatures to calculate the shape of the access cavity (31). In this case a straight line (33) per root canal (3) is defined going through the entrance point (4) of the root canal (3) and fitted through a predetermined portion (32) of the 3D curve (22) associated with said root canal (3). In its limit, the line (33) is fitted through the entire 3D curve (22). The resulting lines (33) for each root canal (3) are extended to the occlusal surface (11) of the tooth (1). The points of emergence (34) of the lines (33) from the occlusal surface (11) are next connected with curves (35) on said surface (11) according to a shortest length principle. This provides an outline (36) on the occlusal surface (11) of the boundaries (28) of the access cavity (31). Optionally an outward offset (37) can be applied to said boundaries (28) to enlarge the access cavity (31), depending on the size of the endodontic instruments to be used. In cases where only a single or two root canals (3) are present, the access cavity (31) may be a single hole (with a given diameter), two separate holes or a slot (i.e. a line cavity with a given width). The walls (38) of the access cavity (31) are given by the respective ruled surfaces generated by connecting line segments between corresponding points on the straight lines (33) extending from the root canals (3). Alternatively the lines (33) fitted through the portion (32) of the 3D curve (22) associated with the respective root canals (3) are extended to the surface (39) of the pulp chamber (2) and the intersection points (40) with said surface (39) are calculated. Said points (40) are connected with curves on the surface (39) according to the shortest path. The thereby outlined boundary (41) is projected onto the occlusal surface (11), thus defining the shape of the access cavity (31). The walls (38) of the access cavity (31) are defined as a sweep of a line parallel to the direction of the projection along the boundary (41). The direction of the projection can for instance be the average direction of the extended lines (33) associated with the respective root canals (3), or perpendicular to a plane (24) fitted through the occlusal surface (11) of the tooth (1) or even randomly specified by the end-user of the system (17). Optionally the boundary (41) outlined on the surface (39) of the pulp chamber (2) can be given an outward offset before projection onto the occlusal surface (11).

According to another embodiment of the present invention, the system (17) uses additional information about the desired prosthetic reconstruction (42) to determine the shape and size of the access cavity (31). As an example the prosthetic restoration (42) of the tooth (1) subsequent to the endodontic treatment can be a dental crown (43). Certain requirements exist for preparing the tooth stump (44) onto which the crown (43) will be cemented. These requirements may not always be compatible with the recommended guidelines for preparing the access cavity (31) to the root canals (3) based on information of the root canals (3) alone. A compromise may be necessary to guarantee the best possible access to the root canals (3) and to allow for the crown (43) to be adequately secured onto the tooth stump (44) subsequent to the endodontic treatment.

Given a desired insertion direction (45) of the crown (43) onto the tooth stump (44), the latter must be prepared in such a manner that there are no undercuts (46) when cementing the crown (43) on top of the tooth stump (44). In addition, the preparation marginal edge (47) of the tooth stump (44) must have a certain profile allowing the smooth transition (i.e. the emergence profile) from the crown (43) to the root (48). Additionally, the stump (44) must be ground down evenly (often more or less conically). This grinding process however must be controlled because of minimum thickness (D) requirements between the surface (49) of the tooth stump (44) and the pulp chamber (2). When the root canals (3) of the tooth (1) to be prepared for receiving the (artificial) crown (43) are oriented substantially askew relative to the original crown (50), the cavity (31) suggested by the system based solely on the principal of straight line access/minimal bending may render it impossible for the clinician to afterwards prepare the stump (44) adequately e.g. because too much material (51) has been removed to gain access to the canals (3). This can be rectified by the system (17). According to a first exemplary approach, two lines are drawn in each of the entrance points (4) of the root canals (3), one line (52) parallel to the predefined insertion direction of the prosthetic element and one line 33) fitted through the 3D curve (or a part thereof) following the respective root canal. Each pair of lines (53) originates in the respective entrance point (4) of the root canals (3). Next, the system (17) calculates for each root canal (3) the respective bisector (54) of said pair of lines (53). Instead of using the extended lines (33) fit though the 3D curves (22) following the root canals (3), the bisectors (54) are now used in the calculation of the shape of the access cavity (31) (as described earlier).

According to yet another embodiment of the current invention, the system (17) allows for the outline (36) of the access cavity (31) on the occlusal surface (11) of the tooth (1) to be transferred into the mouth of the patient. According to one implementation, the system (17) designs a jig (55) that fits onto the occlusal (and/or lingual and buccal) surface (11) of the tooth (1) (and/or the neighbouring teeth), and incorporates the outline (36) of the access cavity (31) e.g. as a central opening (56) in the jig (55). The outline can thus be traced onto the tooth using a medical marker. Said jig may be manufactured using a variety of techniques such as milling, rapid prototyping or the like.

Alternatively, the system (17) outputs via the graphical user interface an occlusal view (57) of the tooth (1) with the boundary (36) of the cavity (31) indicated on a 1:1 scale. This view can for instance be converted into a tool by being printed on transparent plastic (58) and used during the endodontic treatment as an overlay on the tooth (1) to match up with the actual cavity preparation. More advanced systems can be contemplated e.g. where the overlay is projected onto glasses (59) worn during the endodontic treatment and corrected in function of movements of the head relative to the position of the tooth (1). Also navigation systems (60) allowing visualization of the endodontic instruments and the tooth with indication of the boundary (36) of the cavity (31) on the computer screen during the preparation of the access cavity (31) can guide the dental specialist in preparing the access cavity (31) as planned.

Figure 12:
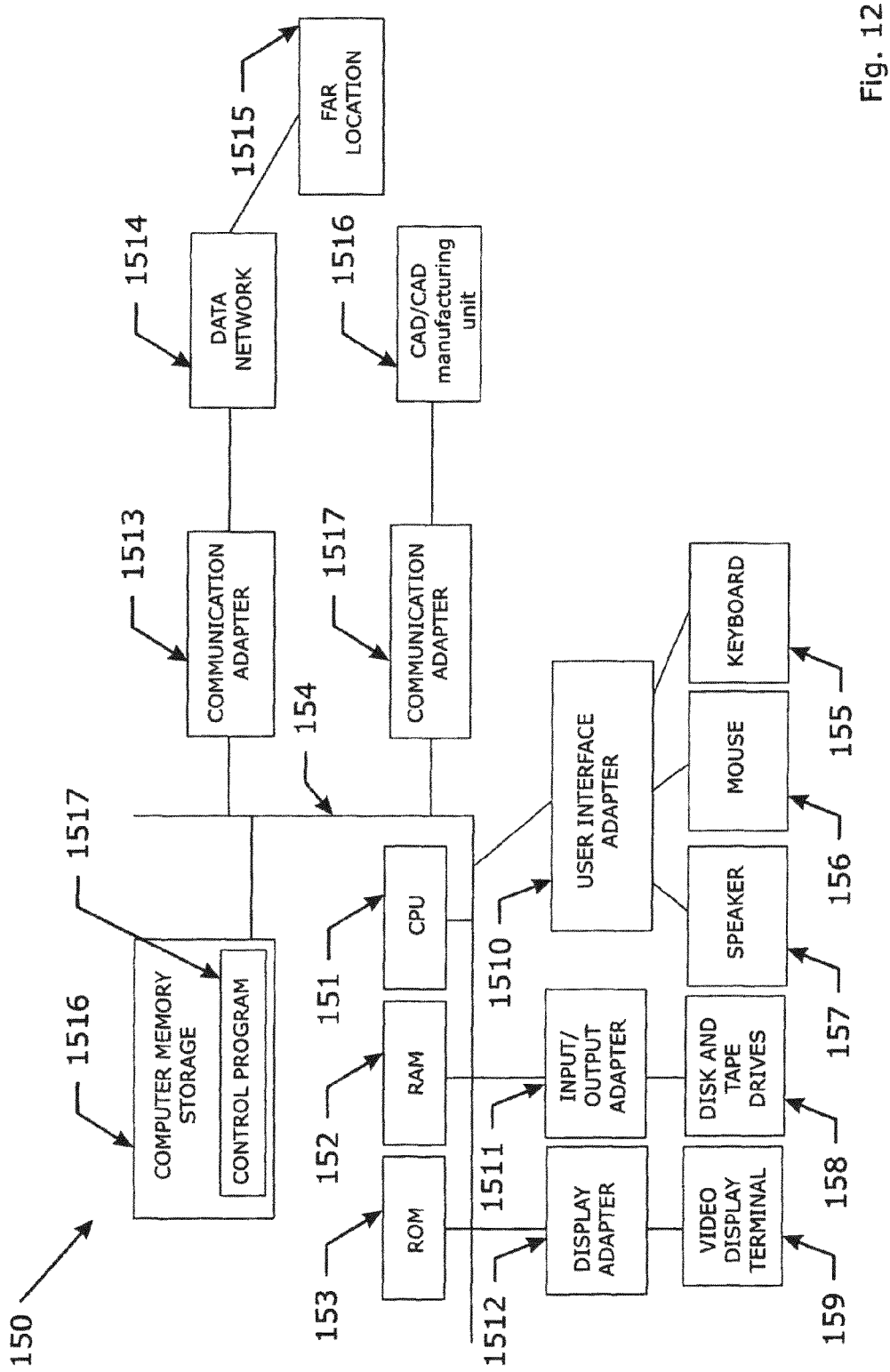
FIG. 12 shows a schematic computer system that can be used with the present invention.

FIG. 12 is a schematic representation of a computing system which can be utilized with the methods and in a system according to the present invention including computer programs such as 3-Matic™ as supplied by Materialise N.V., Leuven, Belgium. A computer 150 is depicted which may include a video display terminal 159, a data input means such as a keyboard 155, and a graphic user interface indicating means such as a mouse 156. Computer 150 may be implemented as a general purpose computer, e.g. a UNIX workstation or a personal computer.

Computer 150 includes a Central Processing Unit ("CPU") 151, such as a conventional microprocessor of which a Pentium processor supplied by Intel Corp. USA is only an example, and a number of other units interconnected via bus system 154. The bus system 154 may be any suitable bus system the above figure is only schematic. The computer 150 includes at least one memory. Memory may include any of a variety of data storage devices known to the skilled person such as random-access memory ("RAM"), read-only memory ("ROM"), and non-volatile read/write memory such as a hard disc as known to the skilled person. For example, computer 150 may further include random-access memory ("RAM") 152, read-only memory ("ROM") 153, as well as a display adapter 1512 for connecting system bus 154 to a video display terminal 159, and an optional input/output (I/O) adapter 1511 for connecting peripheral devices (e.g., disk and tape drives 158) to system bus 154. Video display terminal 159 can be the visual output of computer 150, which can be any suitable display device such as a CRT-based video display well-known in the art of computer hardware. However, with a desk-top computer, a portable or a notebook-based computer, video display terminal 159 can be replaced with a LCD-based or a gas plasma-based flat panel display. Other forms of display can be glasses worn during the endodontic treatment. Computer 150 further includes user interface adapter 1510 for connecting a keyboard 155, mouse 156, and optional speaker 157. The relevant data describing the 3-D model may be input directly into the computer using the keyboard 155 or from storage devices such as 158, after which a processor carries out a method in accordance with the present invention. Any of the results of the method may be transmitted to a further near or remote location, e.g. a printing or CAD/CAM processing facility to manufacture crowns, jigs, tools such as printed plastic templates (as described above) in accordance with the details provided by computer 150.

A printing system or CAD/CAM manufacturing unit 1516 may also be connected via a communications adapter 1517 to bus 154 connecting computer 150 to a data network such as the Internet, an Intranet a Local or Wide Area network (LAN or WAN) or a CAN. The manufacturing unit 1516 may receive a descriptor file suitable for the manufacture of crowns, jigs, tools such as printed plastic templates (as described above), directly from computer 150 running a computer program for establishing the shape of the occlusal access cavity in endodontic treatment in accordance with the present invention or a value or descriptor file derived from such an output of computer 150. Alternatively, the unit 1516 may receive the relevant design data indirectly on a suitable signal storage medium such as a diskette, a replaceable hard disc, an optical storage device such as a CD-ROM or DVDROM, a magnetic tape or similar.

Computer 150 also includes a graphical user interface that resides within machine-readable media to direct the operation of computer 150. Any suitable machine-readable media may retain the graphical user interface, such as a random access memory (RAM) 152, a read-only memory (ROM) 153, a magnetic diskette, magnetic tape, or optical disk (the last three being located in disk and tape drives 158). Any suitable operating system and associated graphical user interface (e.g., Microsoft Windows, Linux) may direct CPU 151. In addition, computer 150 includes a control program 1517 that resides within computer memory storage 1561. Control program 1571 contains instructions that when executed on CPU 151 allow the computer 150 to carry out the operations described with respect to any of the methods of the present invention.

The computer 150 may be used in a computer based method for 3D digital endodontics, 3D imaging equipment being used to digitize an image of an infected tooth or teeth to thereby form image data. The 3D imaging equipment is for generation of volumetric data such as a CT scanner, an MRI scanner, or an ultrasound scanner.

The user interface is preferably adapted to extract the shape of the occlusal access cavity from the image data and visualized on a visual display unit. The user interface is preferably adapted to allow 3D and cross-sectional views of the root canal on coronal, sagittal and/or transverse plans.

Software running on the computer system and is preferably provided for determining the location of root canal orifices by extracting the root canal system from the image data. This step of extracting can be carried out by indicating points along the axis of the root canal in one or multiple slices of the image. The points can be connected and make up a 3D line graph representative of the root canal system of the tooth.

The user interface and the software running on the computer system are preferably adapted to visualize the orifice of each root canal as a point with a distinct colour. Optionally the root canal orifice can be expressed as coordinates in a tooth specific coordinate system.

Those skilled in the art will appreciate that the hardware represented in FIG. 12 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already described.

In the example depicted in FIG. 12, the computer program product for carrying out the method of the present invention can reside in any suitable memory. However, it is important that those skilled in the art will appreciate that the mechanisms of the present invention are capable of being distributed as a computer program product in a variety of forms, and that the present invention applies equally regardless of the particular type of signal bearing media used to actually carry out the distribution. Examples of computer readable signal bearing media include: recordable type media such as floppy disks and CD ROMs, solid state memories, tape storage devices, magnetic disks.

Accordingly, the present invention also includes a software product which when executed on a suitable computing device carries out any of the methods of the present invention. Suitable software can be obtained by programming in a suitable high level language such as C and compiling on a suitable compiler for the target computer processor.

The invention claimed is:

1. A computer based method for defining and representing a shape and geometry of an occlusal access cavity to the tooth roots prior to endodontic treatment, the method comprising:
   loading onto the computer, information of the geometry of a tooth obtained via one or more imaging techniques,
   creation of a three-dimensional computer model of the tooth, including tooth's internal architecture,
   visualisation of the computer model,
   visualisation of the location(s) of the entrance(s) to root canal(s) relative to the tooth's occlusal surface,
   based on the locations of the root canal orifices a shape of the access cavity is calculated by use of a calculating means,
   based on the calculated shape of the access cavity, an outline is calculated on the occlusal surface of the tooth indicating the surface boundaries of the access cavity on the occlusal side of the tooth, and
   visualizing the outline on a display device.

2. The method of claim 1 wherein information about the locations of the root canal orifices is combined with information about the axis of the tooth as a whole or the axes of the individual roots in such a manner that using the latter information to determine a direction is defined according to which the locations are projected onto the surface of the pulp chamber or the occlusal surface of the tooth, the shape of the access cavity being dictated by the shortest path curve connecting the projected points, for example, the envelope around the points, the walls of the access cavity being calculated based on either the root axes information, the direction of the projection, the envelope around the points or a combination of any of these.

3. The method of claim 2 wherein the upper and lower boundaries are defined by the occlusal surface and the surface of the pulp chamber.

4. The method of claim 1 wherein the shape of the access cavity is based on information about the three-dimensional curvature of the root canal(s).

5. The method according to claim 1 further comprising transferring information about the shape of the occlusal access cavity to the tooth of the patient during endodontic treatment.

6. The method of claim 1 wherein the imaging technique provides two-dimensional information, three-dimensional information, surface information, or volumetric information.

7. The method of claim 1 wherein the imaging technique is X-ray, CT, MRI, ultrasound or combinations thereof.

8. The method according to claim 1 wherein the computer model is visualized on a display device such as a computer screen, a projected display, a head mounted display, in sectional views or in a three-dimensional representation such as a surface model or a volume rendering.

9. The method according to claim 2 wherein the location(s) of the entrance(s) to the root canal(s) relative to the tooth's occlusal surface as well as information about the three-dimensional curvature of the root canal(s) are extracted from the computer model of the tooth.

10. The method of claim 9 wherein feature recognition algorithms are used to discriminate the root canal(s} relative to the remainder of the tooth.

11. The method of claim 1 wherein based on the determined locations of the root canal orifices a shape of the access cavity is calculated, wherein the calculation takes into account at least one of the group consisting of:
   i) information of the three-dimensional curvature of the tooth,
   ii) requirements relative to the desired prosthetic restoration of the tooth subsequent to endodontic treatment, and
   iii) requirements/limitations with respect to the use of endodontic instruments.

12. A non-transitory machine readable storage medium storing a computer program, when executed on a computer performs the method of claim 1.

13. The method of claim 1, wherein information about the shape of the occlusal access cavity to the tooth of the patient during endodontic treatment are obtained from visualizing the outline on the display device.

14. The method of claim 1 wherein the display device is a computer screen.

15. A computer based system for defining and representing a shape and geometry of an occlusal access cavity to the tooth roots prior to endodontic treatment, the system comprising:
- data transfer equipment that loads onto a computer, information of the geometry of a tooth obtained via one or more imaging techniques,
- a computer program, that when executed on the computer, creates a three-dimensional computer model of the tooth, including tooth's internal architecture,
- a display device that provides visualisation of the computer model, the system being adapted for visualisation of the location(s) of the entrance(s) to root canal(s) relative to the tooth's occlusal surface, and
- calculating another computer program, that when executed on the computer, calculates a shape of the access cavity based on the locations of the root canal orifices.

16. The system of claim 15 wherein the system is adapted to combine information about the locations of the root canal orifices with information about the axis of the tooth as a whole or the axes of the individual roots in such a manner that using the latter information to determine a direction is defined according to which the locations are projected onto the surface of the pulp chamber or the occlusal surface of the tooth, the shape of the access cavity being dictated by the shortest path curve connecting the projected points, for example, the envelope around the points, the walls of the access cavity calculated based on either the root axes information, the direction of the projection, the envelope around the points or a combination of any of these.

17. The system of claim 16 wherein the upper and lower boundaries are defined by the occlusal surface and the surface of the pulp chamber.

18. The system according to claim 16 further comprising means for extracting from the computer model of the tooth the location(s) of the entrance(s) to the root canal(s) relative to the tooth's occlusal surface as well as information about the three-dimensional curvature of the root canal(s).

19. The system of claim 18 wherein the system is adapted to execute feature recognition algorithms to discriminate the root canal(s) relative to the remainder of the tooth.

20. The system of claim 15 wherein the system is adapted such that based on the calculated shape of the access cavity, an outline is calculated on the occlusal surface of the tooth indicating the surface boundaries of the access cavity on the occlusal side of the tooth, and the display is adapted to visualize this outline.

21. The system of claim 15 wherein the shape of the access cavity is based on information about the three-dimensional curvature of the root canal(s).

22. The system according to claim 15, further comprising means for transferring information about the shape of the occlusal access cavity to the tooth of the patient during endodontic treatment.

23. The system of claim 15 wherein the images of the imaging technique comprise two-dimensional information, three-dimensional information, surface information, or volumetric information.

24. The system of claim 15 wherein the images of the imaging technique are any of X-ray, CT, MRI, ultrasound images.

25. The system according to claim 15 wherein the display is a computer screen, a projected display, a head mounted display, the display being adapted to display in sectional views or in a three-dimensional representation such as a surface model or a volume rendering.

26. The system of claim 15 further comprising means for calculating, based on the determined locations of the root canal orifices, a shape of the access cavity, wherein the calculation takes into account at least one of the group consisting of:
  i) information of the three-dimensional curvature of the tooth,
  ii) requirements relative to the desired prosthetic restoration of the tooth subsequent to endodontic treatment, and
  iii) requirements/limitations with respect to the use of endodontic instruments.

\* \* \* \* \*